US012558076B2

(12) United States Patent (10) Patent No.: US 12,558,076 B2
Goh et al. (45) Date of Patent: Feb. 24, 2026

(54) SAMPLE COLLECTION STICK

(71) Applicant: BIONLIFESCIENCE, INC.,
Namyangju-si (KR)

(72) Inventors: Chang Wook Goh, Namyangju-si
(KR); Joong Hwan Jeong, Bucheon-si
(KR); Bong Yoon Kim, Goyang-si
(KR)

(73) Assignee: BIONLIFESCIENCE, INC.,
Namyangju-si (KR)

( * ) Notice: Subject to any disclaimer, the term of this
patent is extended or adjusted under 35
U.S.C. 154(b) by 447 days.

(21) Appl. No.: 18/245,602

(22) PCT Filed: Sep. 15, 2021

(86) PCT No.: PCT/KR2021/012562
§ 371 (c)(1),
(2) Date: Mar. 16, 2023

(87) PCT Pub. No.: WO2022/060072
PCT Pub. Date: Mar. 24, 2022

(65) Prior Publication Data
US 2023/0329681 A1 Oct. 19, 2023

(30) Foreign Application Priority Data

Sep. 16, 2020 (KR) ........................ 10-2020-0119514
Feb. 5, 2021 (KR) ........................ 10-2021-0017056
(Continued)

(51) Int. Cl.
A61B 10/02 (2006.01)
(52) U.S. Cl.
CPC ..................................... A61B 10/02 (2013.01)

(58) Field of Classification Search
None
See application file for complete search history.

(56) References Cited

U.S. PATENT DOCUMENTS

2007/0093727 A1 4/2007 Feuer et al.
2017/0065261 A1 3/2017 Ching et al.
(Continued)

FOREIGN PATENT DOCUMENTS

CN 204049697 U * 12/2014
EP 0499330 A1 8/1992
(Continued)

OTHER PUBLICATIONS

English Translation KR 20150105281 A, Noblebio Co Ltd, 17
pages, printed on Jul. 10, 2025,. (Year: 2015).*
(Continued)

*Primary Examiner* — Charles A Marmor, II
(74) *Attorney, Agent, or Firm* — NKL Law; Jae Youn
Kim

(57) ABSTRACT

Disclosed is a specimen collection stick including a specimen collection unit, wherein the specimen collection unit includes a plurality of collection disks arranged in a longitudinal direction of a hub, the hub of the specimen collection unit is provided therein with an empty receiving space capable of receiving a specimen formed along a central axis of the hub in the longitudinal direction thereof, whereby it is possible to increase the amount of a specimen that is collected from a subject and to increase the amount of the collected specimen that is dissolved or dispersed in a reagent or a solution from the specimen collection stick.

6 Claims, 9 Drawing Sheets

(30)      Foreign Application Priority Data

Feb. 5, 2021    (KR) ........................ 10-2021-0017061
Sep. 14, 2021    (KR) ........................ 10-2021-0122415

(56)      References Cited

U.S. PATENT DOCUMENTS

| | | | | |
|---|---|---|---|---|
| 2023/0329680 A1* | 10/2023 | Goh | .................. | A61B 10/0045 |
| 2023/0329682 A1* | 10/2023 | Goh | ...................... | A61B 10/02 |
| 2023/0363744 A1* | 11/2023 | Goh | .................. | A61B 10/0051 |
| 2025/0107784 A1* | 4/2025 | Goh | .................. | A61B 10/0051 |

FOREIGN PATENT DOCUMENTS

| | | | | | |
|---|---|---|---|---|---|
| JP | 2004194539 A | | 7/2004 | | |
| KR | 10-2015-0105281 A | | 9/2015 | | |
| KR | 20150105281 A | * | 9/2015 | ....... | B29C 45/14549 |
| KR | 20160062884 A | | 6/2016 | | |

OTHER PUBLICATIONS

English Translation CN 204049697 U, Yang Yanying , 7 pages, printed on Jul. 10, 2025,. (Year: 2014).*

* cited by examiner

10

SAMPLE COLLECTION STICK

TECHNICAL FIELD

The present invention relates to a specimen collection stick, and more particularly to a specimen collection stick capable of scraping a specimen, such as saliva in the oral cavity or the nasal cavity of a subject, thereby collecting the specimen, such as saliva in the oral cavity or the nasal cavity of the subject.

BACKGROUND ART

A microbiological examination is an examination for determining whether a specimen has been contaminated by disease-causing germs. That is, when it is thought that a cause of illness is a microorganism, the microbiological examination is performed in order to establish a method of diagnosing, treating, and preventing the same. The microbiological examination is performed to determine whether a subject has been contaminated by disease-causing germs, such as a colon bacillus, a typhoid bacillus, staphylococcus, and pseudomonas.

In general, a specimen is collected from the body of the subject in order to perform the microbiological examination. The collected specimen is mixed with a reagent or solution for examination, and then examination is performed to determine whether there are disease-causing germs.

In order to collect a specimen, such as saliva or a bodily fluid, from bodily tissue of the subject, a tool called a collection stick, a brush, or a swab is used. That is, the swab for specimen collection is introduced into the body of the subject, a specimen is adhered to the swab, and the swab is withdrawn, whereby the specimen is collected.

In the conventional swab for specimen collection, a circular collection unit is formed at an end of the swab, which is formed in the shape of a bar. The collection unit of the swab is provided with a fiber layer, which is formed by attaching small-sized microfibers to the collection unit. A specimen permeates the fiber layer formed on the collection unit of the conventional swab, and the collection unit of the swab is withdrawn from the subject, whereby the specimen is collected.

In the conventional swab for specimen collection used to collect the specimen, however, it is necessary for the swab to remain inserted in the oral cavity or the nasal cavity of the subject for a predetermined time or more such that saliva or the like permeates the fiber layer, whereby the subject may experience great discomfort. Above all, a part of the fiber layer included in the swab for specimen collection may be separated from the collection unit of the swab and may remain in the body of the subject. When foreign matter, such as the fiber layer, remains in the body of the subject, a medically serious problem may occur. In addition, the amount of the specimen that is collected using the conventional swab is not sufficient, whereby examination accuracy may be lowered.

Therefore, there is a need for technology capable of solving such problems.

DISCLOSURE

Technical Problem

The present invention has been made in view of the above problems, and it is an object of the present invention to provide a specimen collection stick capable of increasing the amount of a specimen that is collected during specimen collection, shortening time necessary for specimen collection, and preventing a problem in which fibers constituting a fiber layer of the conventional swab are separated from the swab.

Technical Solution

A specimen collection stick according to an embodiment of the present invention to accomplish the above object includes a rod-shaped or bar-shaped support unit having a predetermined length and a specimen collection unit located at a front end of the support unit, the specimen collection unit being configured to collect a specimen in a body of a subject that comes into contact with the specimen collection unit, wherein the specimen collection unit includes a hub coupled to the front of the support unit and a plurality of collection disks disposed at an outside of the hub, the collection disks being supported by the hub, the collection disks being arranged in a longitudinal direction of the hub, and the hub may be provided therein with an empty receiving space formed along a central axis of the hub in the longitudinal direction thereof.

The hub may include a rear hub frame coupled to the front portion of the support unit, a front hub frame located spaced apart from the rear hub frame by a predetermined distance so as to be located in front of the rear hub frame, and a plurality of pillars each having a front end connected to the front hub frame and a rear end connected to the rear hub frame, and a hole may be formed in the center of the front hub frame.

Each of the plurality of pillars may be spaced apart from a corresponding one of the plurality of pillars neighboring thereto.

A plurality of collection recesses may be formed in an outer edge of the front hub frame or the rear hub frame.

At least some of the plurality of collection recesses formed in the outer edge of the front hub frame or the rear hub frame may be formed in a direction perpendicular to a central axis of the hub or the support unit in a longitudinal direction thereof.

The hub may be made of a flexible or elastic material.

At least one collection recess having a predetermined depth may be formed in an outer edge of each of the collection disks, the collection recess may be formed in a direction perpendicular to an arbitrary imaginary plane including the central axis of the hub in the longitudinal direction thereof, and each of the collection disks or the hub may be made of a flexible or elastic material.

A coupling projection or coupling protrusion may be formed at an outer circumferential surface of the support unit so as to protrude therefrom, or a lid fastening groove may be formed in the outer circumferential surface of the support unit, such that the support unit can be fixed to a lid of a specimen container configured to receive the specimen collection unit therein by coupling.

Advantageous Effects

A specimen collection stick according to the present invention has effects in that a flocking process, which is required to manufacture the conventional swab for specimen collection, is not necessary, whereby it is possible to reduce the manufacturing cost of the specimen collection stick, and in that there is no fiber layer in the specimen collection stick, whereby it is possible to prevent a problem in which the fiber layer is separated from the specimen collection stick and remains in the body of a subject, unlike the conventional swab for specimen collection, and therefore it is possible to improve examination safety.

Also, in the specimen collection stick according to the present invention, it is possible to increase the amount of the specimen that is collected from the body of the subject, and it is possible to reduce time necessary for specimen collection, since absorption time for which the specimen permeates the fiber layer is not necessary, unlike the conventional swab. Consequently, the specimen collection stick according to the present invention has effects in that it is possible to shorten time necessary for specimen collection, to reduce inconvenience of the subject during specimen collection, and to improve examination accuracy with an increase in amount of the specimen that is collected.

BEST MODE

Figure 1:
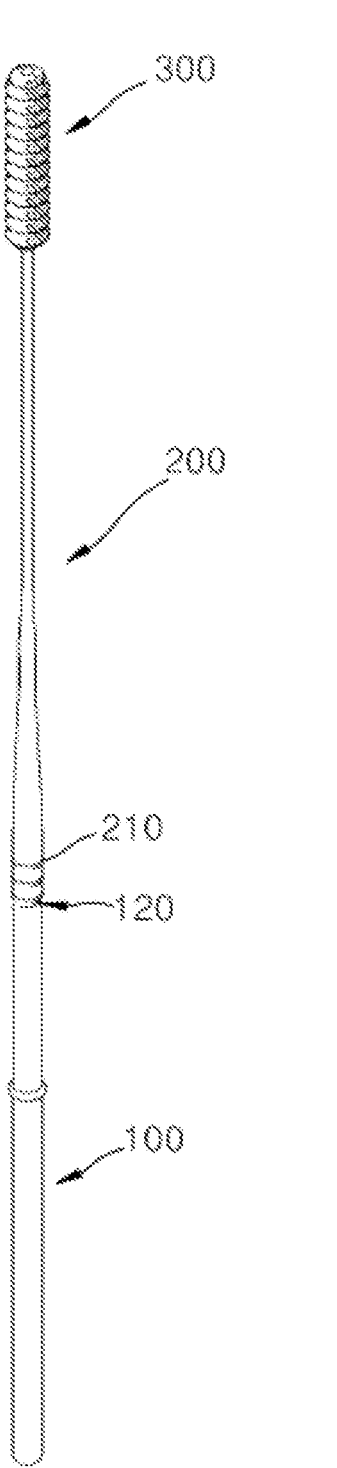
FIG. 1 is a perspective view schematically showing a specimen collection stick according to an embodiment of the present invention.

The present invention may be variously changed and may have several embodiments, and therefore specific embodiments will be described in detail while being illustrated in the drawings. However, the present invention is not limited to the specific embodiments, and it should be understood that the present invention includes all alterations, equivalents, and substitutions falling within the idea and technical scope of the present invention. The present embodiments are provided to more specifically describe the present invention to a person having ordinary skill in the art to which the present invention pertains. Consequently, the shape of each element in the drawings may be exaggerated for clearer description. In describing the present invention, a detailed description of related known technology will be omitted when the same may obscure the subject matter of the present invention.

Although the terms, such as "first" and "second," may be used to describe various elements, the elements must not be defined by the terms. The terms are used only for the purpose of distinguishing one element from another and describing the same so as to be understood.

The terms used in the present invention are used only to describe a specific embodiment, not to define the present invention. Singular forms include plural forms unless mentioned otherwise.

It should be understood that the terms "comprises," "has," etc. specify the presence of stated features, numbers, steps, operations, elements, components, or combinations thereof described in this specification, but do not preclude the presence or addition of one or more other features, numbers, steps, operations, elements, components, or combinations thereof.

Hereinafter, embodiments of the present invention will be described with reference to the accompanying drawings, and the present invention will be described in detail to the extent to which a person having ordinary skill in the art to which the present invention pertains can easily implement the present invention. However, the present invention may be implemented in various different forms and is not limited to the embodiments described herein. Similar parts may be denoted by the same reference numerals throughout the specification.

Hereinafter, embodiments of a specimen collection stick according to the present invention will be described with reference to the drawings.

Figure 2:
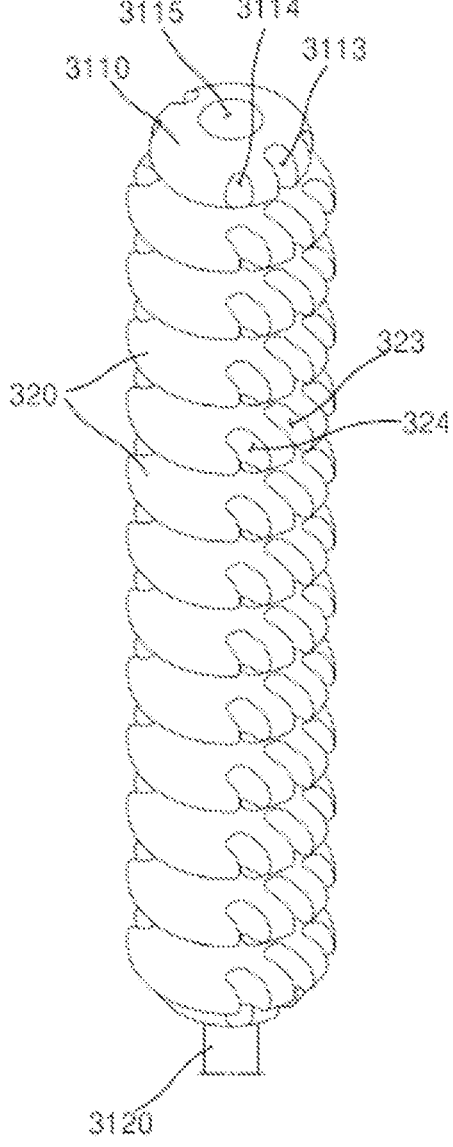
FIG. 2 is a perspective view schematically showing a specimen collection unit of the specimen collection stick according to the embodiment of the present invention.
Figure 3:
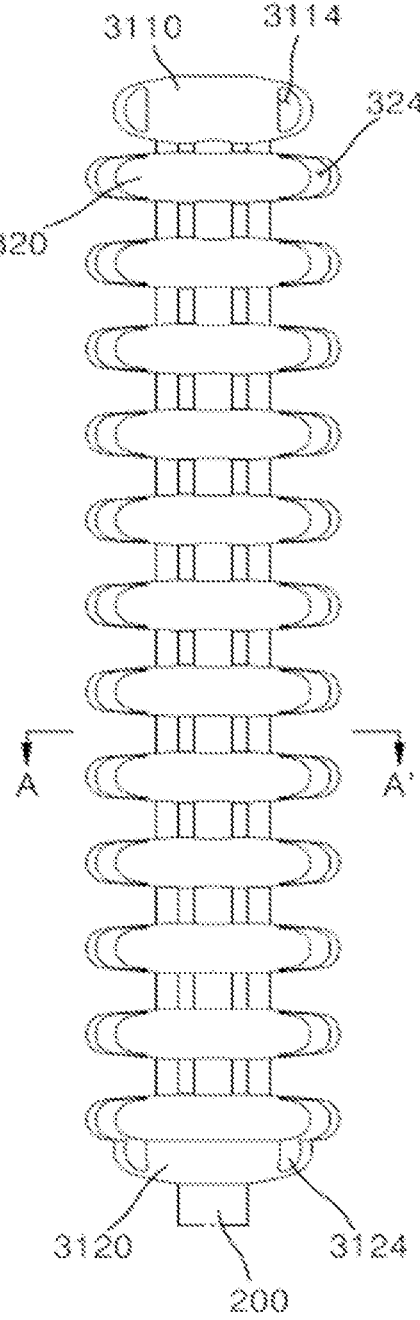
FIG. 3 is a side view schematically showing the specimen collection unit of the specimen collection stick according to the embodiment of the present invention.

FIG. 1 is a perspective view schematically showing a specimen collection stick according to an embodiment of the present invention, FIG. 2 is a perspective view schematically showing a specimen collection unit of the specimen collection stick according to the embodiment of the present invention, and FIG. 3 is a side view schematically showing the specimen collection unit of the specimen collection stick according to the embodiment of the present invention.

Referring to FIGS. 1 to 3, the specimen collection stick according to the first embodiment of the present invention includes a support unit 200 and a specimen collection unit 300, and may further include a handle unit 100.

First, the support unit 200 is formed so as to have a shape, such as a rod or a bar, and has a predetermined length, as shown in the figures. The specimen collection unit 300 is coupled to a front end of the support unit 200. The support unit 200 supports the specimen collection unit 300. The handle unit is connected to the rear of the support unit 200. The support unit 200 supports the specimen collection unit 300 such that the specimen collection unit can be introduced into the body of a subject.

It is sufficient for the support unit 200 to support the specimen collection unit 300 such that the specimen collection unit can be introduced into the body of the subject in order to perform specimen collection, and the support unit is not limited to a specific form.

Furthermore, it is preferable for the support unit 200 to be made of a polymer material that exhibits flexibility and elasticity such that the support unit can return to the original shape thereof while being flexibly deformed by force applied thereto.

Meanwhile, when the specimen collection unit 300 and the support unit 200 of the specimen collection stick 10 are withdrawn from a specimen container (not shown) using a tool, such as a pincette, it is necessary to wash the pincette in advance. In addition, after the support unit 200 of the specimen collection stick 10 is withdrawn from the specimen container using the pincette and the specimen collection unit 300 and the support unit 200 of the specimen collection stick 10 are located at a position intended by an examiner, it is necessary to wash the used pincette again.

Since it is necessary to wash the pincette whenever the pincette is used in the process of withdrawing the specimen collection stick from the specimen container, as described above, specimen examination efficiency is lowered. In order to withdraw the specimen collection unit 300 and the support unit 200 of the specimen collection stick 10 from the specimen container without using the pincette, therefore, the following construction may be provided.

That is, a coupling projection or coupling protrusion 210 may be formed at an outer surface of the support unit 200 so as to protrude from the outer surface thereof such that the coupling projection or coupling protrusion is fixed to a cover or lid of the specimen container by coupling.

The cover or lid (not shown) of the specimen container (not shown) may be provided at an inside thereof with a fixing groove or fitting projection (not shown) configured to allow the support unit 200 of the specimen collection stick to be fixed to the cover or lid (not shown) of the specimen container therethrough. The coupling projection or coupling protrusion 210 of the support unit may be coupled to the fixing groove or fitting projection provided at the inside of the cover or lid of the specimen container by engagement or fitting.

Since the support unit 200 can be fixed to the cover or lid of the specimen container, as described above, it is possible to easily withdraw the support unit 200 from the specimen container together with the cover or lid of the specimen container when the cover or lid is removed from the specimen container without using a tool, such as a pincette, which is preferable.

FIG. 1 shows a ring-shaped coupling projection or coupling protrusion 210 formed on the outer surface of the support unit 200 in a circumferential direction thereof as an illustrative example of the coupling projection or coupling protrusion 210. As shown in FIG. 1, it is also preferable for one or more ring-shaped coupling projections or coupling protrusions 210 to be provided on the outer surface of the support unit 200 at the rear of the support unit 200.

As long as the support unit 200 can be coupled to the cover of the specimen container, as described above, it is possible to improve convenience in use, which is preferable.

As previously described, the handle unit 100 is located at the rear of the support unit 200. That is, a rear end of the support unit 200 is connected to the handle unit 100.

The handle unit 100 is connected to the rear end of the support unit 200, and the handle unit has a predetermined length such that the handle unit can be gripped by the hand or fingers of the examiner.

As shown in the figures, the handle unit 100 is formed in the shape of a rod or a bar having a predetermined length. The handle unit 100 is gripped by the hand or fingers of the examiner. The examiner may perform control such that the specimen collection unit 300 is introduced or inserted into the body of the subject using the handle unit 100.

Consequently, the specimen collection unit 300 may be introduced or inserted into the body of the subject through the oral cavity or the nasal cavity of the subject under control of the examiner using the handle unit 100.

As shown in the figures, it is preferable for a segment groove 120, such as a segment joint, capable of distinguishing between the handle unit 100 and the support unit 200 to be provided between the handle unit 100 and the rear end of the support unit 200. That is, it is preferable for the segment groove 120 to be provided between the handle unit 100 and the support unit 200 such that the handle unit 100 and the support unit 200 can be separated from each other.

After the specimen collection unit 300 is withdrawn from the body of the subject according to the intention of the examiner, who is a user, the specimen collection unit 300 and the support unit 200 are received in the specimen container.

Since it is not necessary to receive the handle unit 100 in the specimen container at this time, it is preferable to separate the handle unit 100 from the support unit 200. As shown in the figures, therefore, it is preferable for the segment joint or segment groove 120 to be provided between the support unit 200 and the handle unit 100 such that the support unit 200 and the handle unit 100 can be separated from each other as needed.

After the support unit 200 and the handle unit 100 are separated from each other, the support unit 200 may be coupled to the cover or lid of the specimen container, as previously described. It is preferable for the coupling projection or coupling protrusion 210 to be formed at an outer circumferential surface of the support unit so as to protrude therefrom or for a lid fastening groove to be formed in the outer circumferential surface of the support unit such that the support unit can be fixed to the cover or lid of the specimen container, in which the specimen collection unit is received, by coupling.

The specimen collection unit 300 is a part that is inserted or introduced into the body of the subject so as to come into contact with a specimen. That is, the specimen collection unit is a part that collects the specimen. The specimen collection unit 300 is located at the front end of the support unit 200 in order to gather or collect a specimen in the body of the subject that comes into contact with the specimen collection unit.

The specimen collection unit 300 includes a hub 310 and a plurality of collection disks 320.

Figure 4:
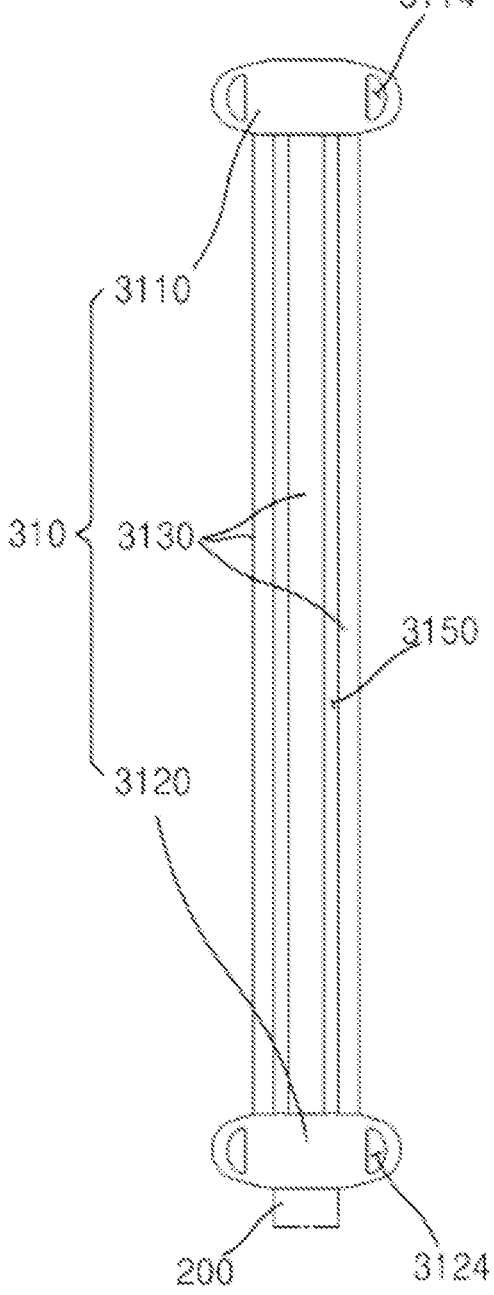
FIG. 4 is a side view schematically showing a hub of the specimen collection unit of the specimen collection stick according to the embodiment of the present invention.

FIG. 4 will be further referred to.

FIG. 4 is a side view schematically showing the hub of the specimen collection unit of the specimen collection stick according to the embodiment of the present invention. That is, FIG. 4 shows the hub 310 of the specimen collection unit excluding the plurality of collection disks 320 for convenience of description and understanding.

Referring further to FIG. 4, the hub 310 is coupled to the front of the support unit 200. It is preferable for the hub 310 and the support unit 200 to be coupled to each other such that a central axis of the hub in a longitudinal direction thereof and a central axis of the support unit 200 in a longitudinal direction thereof are aligned with each other. The hub 310 is coupled to or formed at the support unit 200 such that a front portion of the support unit 200 is inserted into the hub. In addition, the hub 310 supports the plurality of collection disks 320 disposed at the outside thereof.

The plurality of collection disks 320 is disposed at the outside of the hub 310, is supported by the hub 310, and is arranged in the longitudinal direction of the support unit 200.

At least one collection disk 320 is disposed at the outside of the hub 310 such that a specimen brought into contact with the collection disk is withdrawn from the body of the subject in a state of being adhered to or held by the collection disk.

First, the hub 310 of the specimen collection unit 300 will be described in more detail.

As shown in FIG. 4, the hub 310 of the specimen collection unit 300 includes a rear hub frame 3120, a front hub frame 3110, and a plurality of pillars 3130.

The front hub frame 3110, which is a front portion of the hub 310, constitutes the hub 310 together with the rear hub frame 3120 and the pillars 3130.

The front hub frame 3110 is located spaced apart from the rear hub frame 3120, which is coupled to a front portion of the support unit 200, by a predetermined distance so as to be located in front of the rear hub frame.

It is also preferable for a hole 3115 to be formed in the center of the front hub frame 3110. The hole 3115 formed in the center of the front hub frame 3110 communicates with a receiving space 3150, a description of which will follow.

The rear hub frame 3120 is coupled to the front portion of the support unit 200. The rear hub frame 3120, which is a rear portion of the hub 310, constitutes the hub 310 together with the front hub frame 3110 and the pillars 3130. The rear hub frame 3120 is spaced apart from the front hub frame 3110 by a predetermined distance so as to be located behind the front hub frame.

A hole may also be formed in the center of the rear hub frame 3120, in the same manner as the front hub frame 3110. The rear hub frame 3120 may be coupled to the support unit 200 such that the front portion of the support unit 200 is inserted into the hole formed in the center of the rear hub frame 3120.

Since the rear hub frame 3120 is coupled to the support unit 200, as described above, the hub 310 may be supported by the support unit 200.

A front end of the pillar 3130 is connected to the front hub frame 3110, and a rear end of the pillar is connected to the rear hub frame 3120. A plurality of pillars 3130 is disposed between the front hub frame 3110 and the rear hub frame 3120. It is preferable for each of the plurality of pillars 3130 to be spaced apart from a corresponding one of the pillars 3130 neighboring thereto by predetermined distance. The plurality of pillars 3130 may be disposed between the front hub frame 3110 and the rear hub frame 3120 in rotational symmetry or axial symmetry with respect to the central axis of the hub 310 in the longitudinal direction thereof.

The hub 310 is provided with an empty receiving space 3150, which is formed in the hub 310 along the central axis of the hub in the longitudinal direction thereof, which connects the center of the front hub frame 3110 and the center of the rear hub frame 3120 to each other.

A specimen that is collected may be received in the empty receiving space 3150 provided in the hub 310. That is, since the plurality of pillars 3130 is spaced apart from each other, a specimen may be introduced into and received in the receiving space 3150 provided in the hub 310 from the outside of the hub 310.

Consequently, the specimen collection stick 10 according to the present invention is capable of collecting a larger amount of a specimen than a conventional specimen collection stick having no receiving space 3150 in the hub 310.

A plurality of collection recesses 3113, 3114, and 3124 configured to receive a specimen in order to collect the specimen may be formed in an outer edge of the front hub frame 3110 or the rear hub frame 3120, which is also preferable.

When the plurality of collection recesses 3113, 3114, 3123, and 3124 is formed in the outer edge of the front hub frame 3110 or the rear hub frame 3120, it is preferable for at least some of the plurality of collection recesses 3113, 3114, and 3124 to be formed in a direction perpendicular to the central axis of the hub 310 or the support unit 200 in the longitudinal direction thereof.

In other words, it is preferable for the collection recesses 3113, 3114, and 3124 formed in the outer edge of the front hub frame 3110 or the rear hub frame 3120 to be formed in a direction perpendicular to an arbitrary imaginary plane including the central axis of the hub in the longitudinal direction thereof.

Here, the plurality of collection recesses 3113, 3114, and 3124 formed in the outer edge of the front hub frame 3110 or the rear hub frame 3120 may be disposed symmetrically with respect to the arbitrary imaginary plane.

In addition, the plurality of collection recesses 3113, 3114, and 3124 formed in the outer edge of the front hub frame 3110 or the rear hub frame 3120 may be formed so as to have a predetermined depth or a predetermined width. For example, the neighboring collection recesses 3113, 3114, and 3124 may have the same depth or the same width, and the neighboring collection recesses 3113, 3114, and 3124 may have different depths or different widths.

It is preferable for the hub 310 to be made of a flexible or elastic material. That is, the hub may be made of a polymer material that exhibits flexibility and elasticity or an elastomer material.

Next, the collection disk 320 will be described with further reference to FIG. 5.

Figure 5:
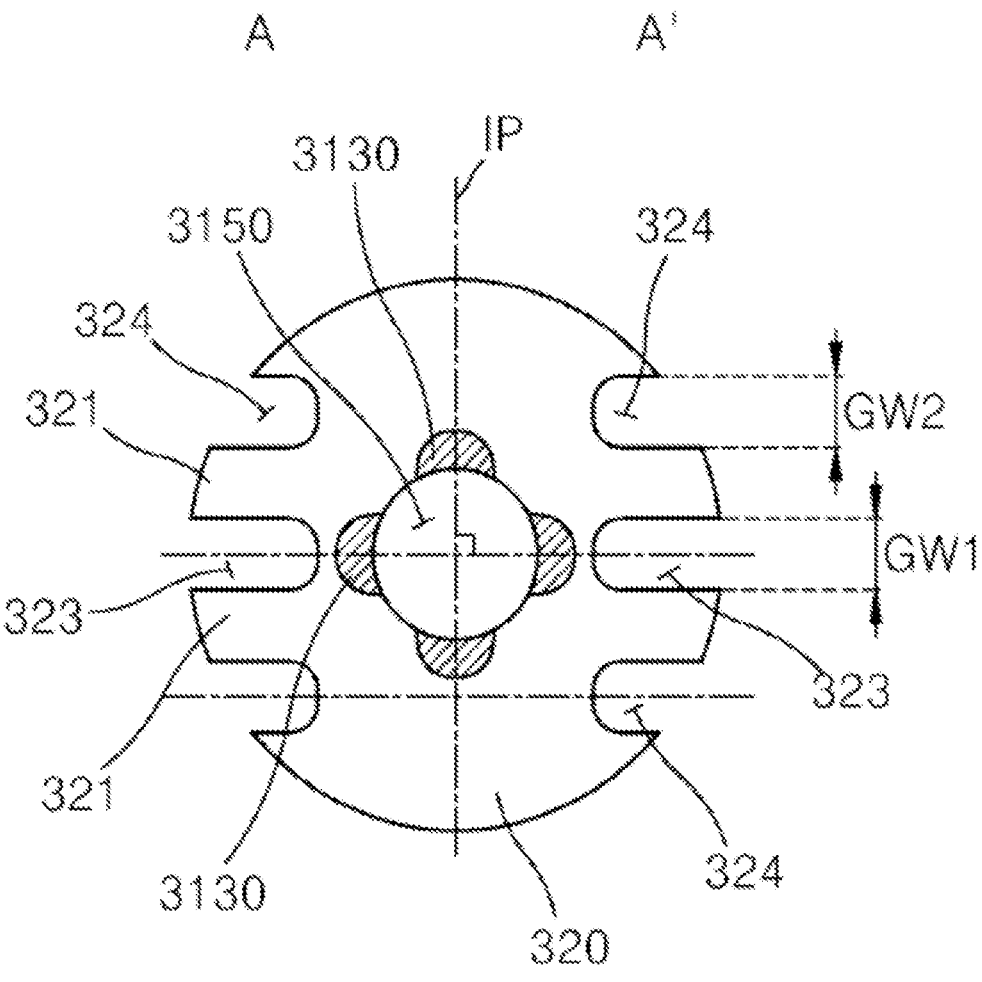
FIG. 5 is a sectional view schematically showing the specimen collection unit of the specimen collection stick according to the embodiment of the present invention.

FIG. 5 is a sectional view schematically showing the specimen collection unit of the specimen collection stick according to the embodiment of the present invention.

Referring further to FIG. 5, the specimen collection unit 300 includes a plurality of collection disks 320 arranged in the longitudinal direction of the support unit 200 or the hub 310, as previously described.

That is, the specimen collection unit 300 includes a plurality of collection disks 320 arranged in the longitudinal direction of the hub, the collection disks 320 being configured to allow a specimen brought into contact therewith to be adhered thereto or to be held thereby and to be withdrawn from the body of the subject in that state. It is preferable for the plurality of collection disks 320 to be spaced apart from each other by a predetermined distance. Also, it is preferable for the center of each of the collection disks 320 to be on the central axis of the hub in the longitudinal direction thereof.

Each of the collection disks 320 is formed in the shape of a plate having at least one curved or flat side surface. In addition, the edge of the collection disk 320 is circular or oval. The collection disk 340 may have a disk or circular shape.

The collection disks 320 may be formed around the hub 310 at the outside of the hub 310, i.e. the pillars 3130. The collection disks 320 thus formed are supported by the hub 310.

The hub 310, which supports the collection disks 320, is coupled to the front portion of the support unit 200. Consequently, the hub 310 supports the collection disks 320 while being supported by the support unit 200. When the collection disks 320 are included in the specimen collection unit 300, as described above, the surface area of the specimen collection unit 300 that comes into contact with a specimen is increased. Consequently, the amount of a specimen that is collected is increased.

A gap, through which the pillars 3130 of the hub 310 are exposed outwards, is provided between neighboring ones of the collection disks 320. Even in the gap, the specimen collection unit may come into contact with a specimen in the body of the subject, and the specimen may be withdrawn from the body of the subject in a state of being held in the gap.

In short, a specimen may be adhered and held by the pillars 3130 of the hub between neighboring ones of the collection disks 320, and the specimen may be withdrawn from the body of the subject in that state.

Each of the collection disks 320 is flexible and elastic. Consequently, each of the plurality of collection disks 320 abuts bodily tissue in the body of the subject. The examiner swings the specimen collection unit 300 in the body of the subject using the handle unit 100 such that the collection disks 320 can scrape or sweep the bodily tissue in which the specimen is present while abutting the bodily tissue. As a result, the specimen is adhered to the surface of each of the collection disks 320 or is held in the gap between the neighboring ones of the collection disks 320.

That is, the specimen is adhered to the surface of each of the collection disks 320 or is held in the gap between the neighboring ones of the collection disks 320 in the state in which the specimen collection unit 300 is inserted in the body of the subject, whereby the specimen remains on the specimen collection unit 300 when the specimen collection unit 300 is withdrawn from the body of the subject.

The gap between the neighboring ones of the collection disks 320 may also be referred to as a collection space or a collection gap.

Also, in at least some of the plurality of collection disks 320, it is also preferable for neighboring ones of the collection disks 320 to have different diameters or different long radii. Of course, all of the plurality of collection disks 320 may also have the same diameter or the same long radius.

In the specimen collection unit 300, therefore, the specimen brought into contact with the collection disks 320 or the hub 310 may be maintained in a state of being held by or adhered to the collection disks 320.

As shown in the figures, one or more collection recesses 323 and 324 each having a predetermined depth are formed in an outer edge of each of the collection disks 320. It is preferable for the collection recesses 323 and 324 to be formed in a direction perpendicular to an arbitrary imaginary plane IP including the central axis of the hub in the longitudinal direction thereof.

At least some of the one or more collection recesses 323 may be formed in a direction perpendicular to the central axis of the hub 310 or the support unit 200 in the longitudinal direction thereof.

Here, at least some of the one or more collection recesses 323 may be formed in a direction in which neighboring collection recesses 323 and 324 are parallel to each other within a predetermined error range. In other words, the longitudinal directions of the collection recesses 323 and 324 formed so as to neighbor each other may be parallel to each other.

For reference, in FIG. 5, reference numeral 321 indicates a part of each of the collection disks 320 at which the collection recesses 323 and 324 are not formed, i.e. a part between neighboring collection recesses 323 and 324.

Among the collection recesses 323 and 324 formed in the direction perpendicular to the arbitrary imaginary plane IP including the central axis of the hub 310 in the longitudinal direction thereof, the collection recesses 323, the depth direction or the center line of each of which extends through the central axis of the hub 310 in the longitudinal direction thereof, may be referred to as first collection recesses 323.

In addition, the collection recesses 324 respectively neighboring the first collection recesses 323 or the collection recesses 324, the depth direction or the center line of each of which does not intersect the central axis of the hub 310 in the longitudinal direction thereof, may be referred to as second collection recesses 324.

Each first collection recess 323 and each second collection recess 324 may have predetermined depths. Consequently, the depth of the first collection recess 323 and the depth of the second collection recess 324 may be equal to each other or different from each other. The first collection recesses 323 and the second collection recesses 324 may be formed in the outer edge of each of the collection disks 320 in the state in which the depth of each first collection recess 323 and the depth of each second collection recess 324 are preset as needed.

The width GW1 of the first collection recess 323 and the width GW2 of the second collection recess 324 may have predetermined values. The width GW1 of the first collection recess 323 and the width GW2 of the second collection recess 324 may be equal to each other or different from each other. The collection recesses 323 and 324 may be formed in the state in which the widths GW1 and GW2 are set as needed by design.

A specimen may be received and held in the one or more collection recesses 323 and 324 formed in the outer edge of each of the collection disks 320.

Even when the one or more collection recesses 323 and 324 are formed in each of the collection disks 320, as described above, the amount of the specimen that is collected from the body of the subject is increased, in the same manner as the above description. It is preferable for the first collection recesses 323 or the second collection recesses 324 to be formed in the outer edge of each of the collection disks 320.

The structure in which the one or more collection recesses 323 and 324 are formed in each of the collection disks 320, as described above, may also be provided, which is also preferable.

In the specimen collection stick according to the embodiment of the present invention, as described above, the amount of the specimen that is collected by the collection disks 320 included in the specimen collection unit 300 is greater than the amount of the specimen collected by the conventional swab for specimen collection.

Consequently, it is possible to increase the amount of the specimen that is collected from the subject and to increase the amount of the collected specimen that is dissolved or dispersed in a reagent or a solution from the specimen collection stick.

It is preferable for the thickness of each collection disk 320 from one end of the collection disk 320 connected to the pillars 3130 of the hub 310 to the other end of the collection disk 320, which is the outer edge of the collection disk 320, to be uniform. In addition, as shown in FIG. 6, it is also preferable for the thickness of a part of each collection disk to be reduced.

Figure 6:
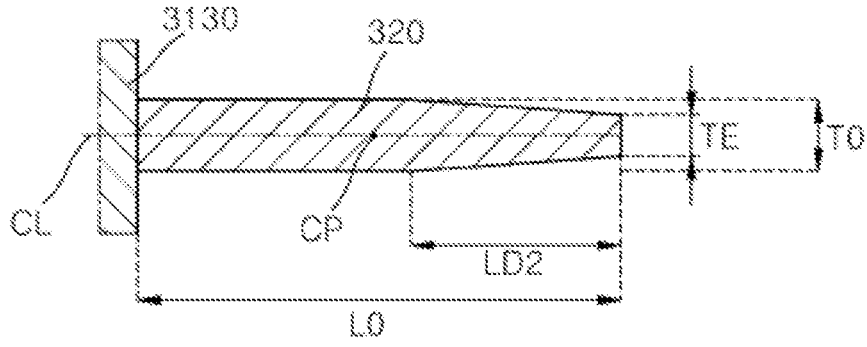
FIG. 6 is a side view schematically showing a pillar and a collection disk of the specimen collection stick according to the embodiment of the present invention.

FIG. 6 is a partial side sectional conceptual view schematically showing the hub and the collection disk of the specimen collection unit of the specimen collection stick according to the embodiment of the present invention. That is, this figure is a conceptual view showing a plane including a point on the outer edge of the collection disk 320 and the central axis of the hub 310 in the longitudinal direction thereof as a side sectional view.

In FIG. 6, one side of the collection disk 320 is connected to the pillar 3130 of the hub 310. Here, the outer edge of the collection disk 320 is the other end of the collection disk 320. The collection disk 320 may also be formed such that at least a part LD2 of a longitudinal length section L0 has a thickness (T0→TE) gradually reduced to the other side of the collection disk.

Here, reference symbol T0 indicates the thickness T0 at the point of the at least a part LD2 of the longitudinal length section L0 of the collection disk 320 from which the thickness starts to be gradually reduced to the other side of the collection disk, and reference symbol TE indicates the thickness TE at the other end of the collection disk 320.

That is, it is preferable for the at least a part LD2 of the longitudinal length section L0 to be formed such that the thickness is reduced from T0 to TE. In other words, it is preferable for the thickness to be tapered.

As described above, it is preferable for the collection disk 320 to be formed such that the lateral width WD or the thickness (T0→TE) of the at least a part LD2 of the longitudinal length section L0 is gradually reduced to the other side of the collection disk.

It is preferable for the thickness of the collection disk 320 to range from 0.1 mm to 1 mm, more preferably from 0.2 mm to 0.8 mm.

The collection disk 320 may be made of a polymer material that exhibits flexibility and elasticity or an elastomer.

When the collection disk 320 is formed such that the thickness is gradually reduced to the outer edge of the collection disk, i.e. the other end of the collection disk, as described above, the outer edge of the collection disk 320 is capable of holding a specimen brought into contact therewith while returning to the original state thereof after being flexibly bent, which is preferable.

Since the specimen brought into contact with the collection disks 320 disposed around the hub 310 or adhered thereto remains held between the collection disks 320 while the specimen is inhibited from being separated from the collection disks 320, as described above, it is possible to further increase the amount of the specimen that is collected, compared to the conventional art.

Furthermore, the specimen brought into contact with the collection recesses 323 and 324 formed at the outside of each of the collection disks 320 or adhered thereto may remain held in the collection recesses 323 and 324 while the specimen is inhibited from being separated therefrom, whereby it is possible to increase the amount of the specimen that is collected.

It is preferable for the collection disks 320 to be manufactured by molding such that each of the collection disks has a size set depending on the part of the body of the subject into which the collection disks are inserted, such as the nasal cavity, the oral cavity, the anus, or the cervix. The specimen collection unit 300 including the collection disks 320 and the hub 310 may be made of a polymer material that exhibits flexibility and elasticity or an elastomer.

For reference, a modified embodiment may also be provided as follows.

Figure 7:
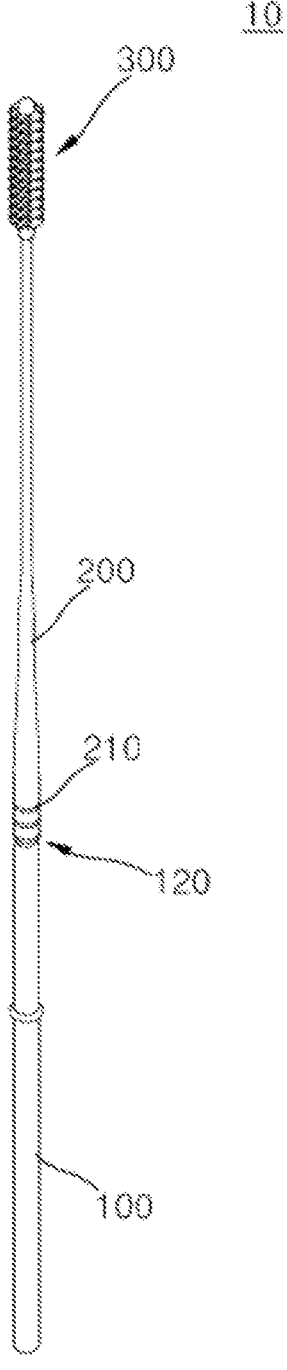
FIG. 7 is a perspective view schematically showing a specimen collection stick according to a modified embodiment of the present invention.
Figure 8:
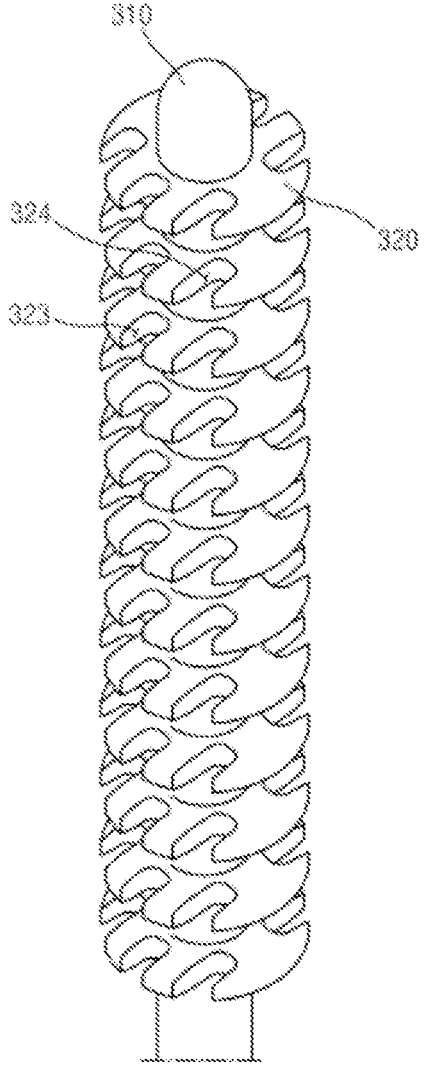
FIG. 8 is a perspective view schematically showing a specimen collection unit of the specimen collection stick according to the modified embodiment of the present invention.
Figure 9:
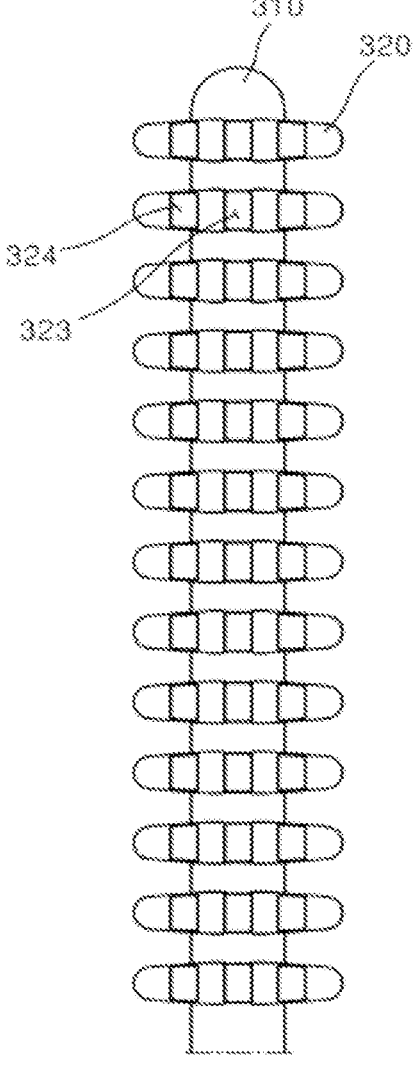
FIG. 9 is a side view schematically showing the specimen collection unit of the specimen collection stick according to the modified embodiment of the present invention. FIG. is a side view schematically showing a specimen collection unit of a specimen collection stick according to another embodiment of the present invention.
Figure 10:
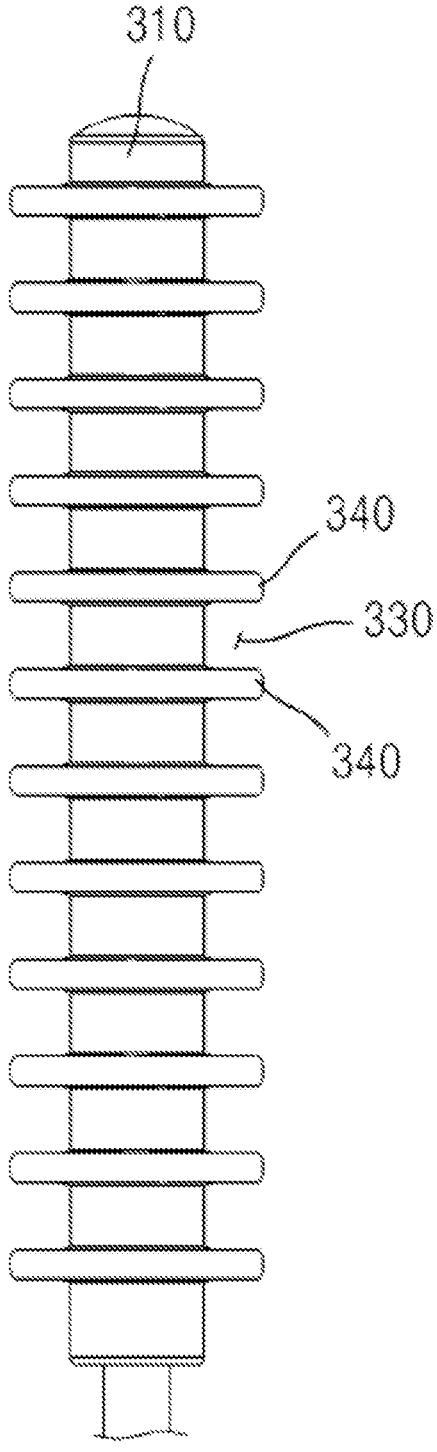

FIG. 7 is a perspective view schematically showing a specimen collection stick according to a modified embodiment of the present invention, FIG. 8 is a perspective view schematically showing a specimen collection unit of the specimen collection stick according to the modified embodiment of the present invention, and FIG. 9 is a side view schematically showing the specimen collection unit of the specimen collection stick according to the modified embodiment of the present invention. In addition, FIG. 10 is a side view schematically showing a specimen collection unit of a specimen collection stick according to another embodiment of the present invention.

Referring to FIGS. 7 to 9, the specimen collection stick according to the modified embodiment of the present invention includes a support unit 200 and a specimen collection unit 300, and may further include a handle unit. Here, a description of the support unit 200 and the specimen collection unit 300 is identical to the description thereof given with reference to FIGS. 1 to 3, and therefore a description of the support unit and the specimen collection unit may be substituted by the above description.

The specimen collection unit 300 is a part that is inserted or introduced into the body of a subject so as to come into contact with a specimen. That is, the specimen collection unit is a part that collects the specimen. The specimen collection unit 300 is located at a front end of the support unit 200 in order to gather or collect a specimen in the body of the subject that comes into contact with the specimen collection unit.

As shown in FIG. 9, the specimen collection unit 300 includes a hub 310 and a plurality of collection disks 320. Of course, as shown in FIG. 10, the specimen collection unit may include a hub 310 and a plurality of collection disks 340.

The specimen collection unit 300 is coupled to the front of the support unit 200. It is preferable for the hub 310 and the support unit 200 to be coupled to each other such that a central axis of the hub in a longitudinal direction thereof is aligned with a central axis of the support unit 200 in a longitudinal direction thereof. The hub 310 is coupled to or formed at the support unit 200 such that a front portion of the support unit 200 is inserted into the hub 310. The hub 310 supports the plurality of collection disks 320 disposed at the outside thereof.

The plurality of collection disks 320 is disposed at the outside of the hub 310, is supported by the hub 310, and is arranged in the longitudinal direction of the hub.

The plurality of collection disks 320, which is arranged in the longitudinal direction of the hub, is disposed at the outside of the hub 310 such that a specimen brought into contact with the collection disks is withdrawn from the body of the subject in a state of being adhered to or held by the collection disks.

It is preferable for the hub 310 to be made of a flexible or elastic material. That is, the hub may be made of a polymer material that exhibits flexibility and elasticity or an elastomer material.

As shown in the figures, the hub 310 may be formed in the shape of a bar having a circular section; however, the present invention is not limited thereto.

As shown in FIG. 9 or 10, the collection disks 320 or 340 may be formed around the hub 310 on an outer circumferential surface of the hub 310. The collection disks 320 or 340 thus formed are supported by the hub 310.

In the specimen collection unit 300, the specimen brought into contact with the collection disks 320 or 340 or the hub 310 may be maintained in a state of being held by or adhered to the collection disks 320 or 340. For reference, in FIG. 10, reference numeral 330 indicates a space 330 between neighboring ones of the collection disks 340, in which a specimen is held and received.

No collection recess is formed in an outer edge of each of the collection disks 340, as shown in FIG. 10, whereas collection recesses are formed in an outer edge of each of the collection disks 320, as shown in FIG. 9.

As shown in FIGS. 7 to 9, one or more collection recesses 323 and 324 are formed in the outer edge of each of the collection disks 320 so as to have predetermined depths.

It is preferable for the collection recesses 323 and 324 to be formed in a direction perpendicular to an arbitrary imaginary plane including the central axis of the hub in the longitudinal direction thereof. A description of the collection recesses 323 and 324 is identical to the description thereof previously given with reference to FIG. 5, and therefore a description of the collection recesses may be substituted by the above description. In addition, a description of the thickness of each of the collection disks 320 is identical to the description thereof previously given with reference to FIG. 6, and therefore a description of the thickness of each of the collection disks may be substituted by the above description Meanwhile, pluralities of concave parts and convex parts corresponding to the collection recesses may also be alternately formed at the outer edge of each of the collection disks. In other words, pluralities of concave parts and convex parts constituting a plurality of collection recesses may be alternately formed at the outer edge of each of the collection disks, which is preferable. Here, the concave parts and convex parts or the collection recesses may have various shapes, and the shape thereof is not limited to a specific shape.

When the plurality of collection recesses or the pluralities of concave parts and convex parts are formed at each of the collection disks, as described above, the surface area of the outer edge of each of the collection disks is increased, which may assist in increasing the amount of the specimen that is collected.

A specimen may be held in the concave parts, which are concavely formed so as to serve as the collection recesses, among the concave parts and the convex parts of each of the collection disks. Here, the specimen may be held due to viscosity of the specimen, elasticity of each of the flexible collection disks, and an increase in surface area of each of the collection disks 320 that contacts the specimen.

For example, curved concave parts and curved convex parts may be alternately formed at the outer edge of each of the collection disks in the shape of a sine wave, or angular concave parts and angular convex parts may be alternately formed at the outer edge of each of the collection disks in the shape of a square wave, which is also preferable.

In the specimen collection stick according to the modified embodiment of the present invention, as described above, the amount of the specimen that is collected in the gap between neighboring ones of the collection disks and the collection recesses is increased, whereby the amount of the specimen is greater than the amount of the specimen collected by the conventional swab for specimen collection.

As described above, it is possible to increase the amount of the specimen that is collected from the subject and to increase the amount of the collected specimen that is dissolved or dispersed in a reagent or a solution from the specimen collection stick.

In the specimen collection stick according to the embodiment of the present invention, as previously described, a specimen that is collected may be received in the receiving space of the hub, and the amount of the specimen collected in the gap between the plurality of collection disks is greater than the amount of the specimen collected by the conventional swab for specimen collection.

Consequently, it is possible to increase the amount of the specimen that is collected from the subject and to increase the amount of the collected specimen that is dissolved or dispersed in a reagent or a solution from the specimen collection stick.

As can be seen from the above description, the specimen collection stick according to the present invention has advantages in that a flocking process, which is required to manufacture the conventional swab for specimen collection, is not necessary, whereby it is possible to reduce the manufacturing cost of the specimen collection stick, and in that there is no fiber layer in the specimen collection stick, whereby it is possible to prevent a problem in which the fiber layer is separated from the specimen collection stick and remains in the body of the subject, unlike the conventional swab for specimen collection.

In addition, the specimen collection stick according to the present invention has advantages in that it is possible to increase the amount of the specimen that is collected from the subject, compared to the conventional swab, to increase the amount of the collected specimen that is dissolved or dispersed in a reagent or a solution from the specimen collection stick, and to improve examination accuracy with an increase in amount of the specimen that is collected.

Furthermore, the specimen collection stick according to the present invention has advantages in that it is possible to shorten time necessary for specimen collection and to reduce inconvenience of the subject during specimen collection. In addition, the specimen collection unit, which is inserted into the oral cavity or the nasal cavity of the subject, is made of a polymer material that exhibits flexibility and elasticity or an elastomer material, whereby it is possible to reduce inconvenience of the user.

Although the present invention has been described in detail based on the embodiment with reference to the accompanying drawings, as described above, the embodiments are merely provided to describe the present invention, and therefore it should be understood that the present invention is not limited to the embodiments, and the scope of rights of the present invention should be interpreted by the following claims and equivalent thereto.

100: Handle unit
200: Support unit
300: Specimen collection unit
310: Hub

The invention claimed is:

1. A specimen collection stick comprising:

a rod-shaped or bar-shaped support unit having a predetermined length; and a specimen collection unit located at a front end of the support unit, the specimen collection unit being configured to collect a specimen in a body of a subject that comes into contact with the specimen collection unit, wherein:

the specimen collection unit comprises:

a hub coupled to the front end of the support unit; and a plurality of collection disks disposed at an outside of the hub, the collection disks being supported by the hub, the collection disks being arranged in a longitudinal direction of the hub, the hub is provided therein with an empty receiving space formed along a central axis of the hub in the longitudinal direction thereof, the hub comprises:

a rear hub frame coupled to the front end of the support unit;

a front hub frame located spaced apart from the rear hub frame by a predetermined distance so as to be located in front of the rear hub frame; and a plurality of pillars each having a front end connected to the front hub frame and a rear end connected to the rear hub frame, and a hole is formed in a center of the front hub frame.

2. The specimen collection stick according to claim 1, wherein a plurality of collection recesses is formed in an outer edge of the front hub frame or the rear hub frame.

3. The specimen collection stick according to claim 2, wherein at least one of the plurality of collection recesses formed in the outer edge of the front hub frame or the rear hub frame are formed in a direction perpendicular to a central axis of the hub or the support unit in a longitudinal direction thereof.

4. The specimen collection stick according to claim 1, wherein the hub is made of a flexible or elastic material.

5. The specimen collection stick according to claim 1, wherein at least one collection recess having a predetermined depth is formed in an outer edge of each of the collection disks, the collection recess is formed in a direction perpendicular to an arbitrary imaginary plane comprising the central axis of the hub in the longitudinal direction thereof, and each of the collection disks or the hub is made of a flexible or elastic material.

6. The specimen collection stick according to claim 1, wherein a coupling projection or coupling protrusion is formed at an outer circumferential surface of the support unit so as to protrude therefrom, or a lid fastening groove is formed in the outer circumferential surface of the support unit, such that the support unit can be fixed to a lid of a specimen container configured to receive the specimen collection unit therein by coupling.

* * * * *